US006024694A

United States Patent [19]
Goldberg et al.

[11] Patent Number: 6,024,694
[45] Date of Patent: Feb. 15, 2000

[54] HUMIDIFIER FOR A THERMAL SUPPORT APPARATUS

[75] Inventors: Charles Goldberg, Cincinnati, Ohio; Douglas K. Smith, Batesville, Ind.; Floyd G. Speraw, Anderson, S.C.

[73] Assignee: Hill-Rom, Inc., Batesville, Ind.

[21] Appl. No.: 08/926,383

[22] Filed: Sep. 9, 1997

Related U.S. Application Data

[63] Continuation-in-part of application No. 08/532,963, Sep. 25, 1995, Pat. No. 5,759,149.

[51] Int. Cl.⁷ ..................................................... A61G 11/00
[52] U.S. Cl. ................................................................ 600/22
[58] Field of Search .......................................... 600/21–22

[56] References Cited

U.S. PATENT DOCUMENTS

| | | |
|---|---|---|
| 3,158,150 | 11/1964 | Croasdaile . |
| 3,187,744 | 6/1965 | Dorsak et al. . |
| 3,335,713 | 8/1967 | Grosholz et al. . |
| 3,511,162 | 5/1970 | Truhan . |
| 3,821,947 | 7/1974 | Schossow . |
| 4,161,172 | 7/1979 | Pickering . |
| 4,361,137 | 11/1982 | Grosholz . |
| 4,750,474 | 6/1988 | Dukhan et al. . |
| 4,796,605 | 1/1989 | Sasaki et al. . |
| 4,846,783 | 7/1989 | Koch et al. . |
| 4,936,824 | 6/1990 | Koch et al. . |
| 5,162,038 | 11/1992 | Wilker . |
| 5,224,923 | 7/1993 | Moffett et al. . |
| 5,242,375 | 9/1993 | McDonough . |
| 5,336,156 | 8/1994 | Miller et al. . |
| 5,453,077 | 9/1995 | Donnelly et al. . |
| 5,498,229 | 3/1996 | Barsky et al. . |
| 5,539,854 | 7/1996 | Jones et al. . |
| 5,616,115 | 4/1997 | Gloyd et al. . |

FOREIGN PATENT DOCUMENTS

| | | |
|---|---|---|
| 2061704 | 7/1979 | Germany . |
| 49-122184 | 11/1974 | Japan . |
| 2175213 | 11/1986 | United Kingdom . |
| 2067077 | 7/1987 | United Kingdom . |

OTHER PUBLICATIONS

"Stabilet® From Hill–Rom®" Product Brochure, six pages, 1992.
"Stabilet CC™ From Hill–Rom®" Product Brochure, six pages, 1992.
"The Stabilet™ Freestanding Warmer and Clinical Bassinet From Hill–Rom™" Product Brochure, four pages, 1993.
"A Hill–Rom Solution", Stabilet 2000C, Stabilet CC, Stabilet Freestanding Infant Warmer Accessories Product Borchure, eight pages, 1995.
"Isolette™ Infant Incubator . . . The Essence of Incubation", Air–Shields, Inc. Product Brochure, eight pages, 1996.
"Infa–Care 2000", Infa–Care, Inc. Product Brochure, six pages, date unknown, 1972.

*Primary Examiner*—John P. Lacyk
*Attorney, Agent, or Firm*—Barnes & Thornburg

[57] ABSTRACT

A humidifier module is provided for a patient support apparatus which includes an opening into which the module is inserted, an electrical service connector, an air inlet port, and an air outlet port. The humidifier module includes a water reservoir and a heater configured to heat water in the reservoir. An air chamber with an air inlet port and an air exhaust port for mating with air inlet and outlet ports of the patient support apparatus and an electrical connector for mating with the electrical service connector of the patient support apparatus is included in the humidifier module. When the humidifier module is inserted into the patient support apparatus, the patient support apparatus is provided with a humidified environment for a patient.

71 Claims, 8 Drawing Sheets

HUMIDIFIER FOR A THERMAL SUPPORT APPARATUS

RELATED APPLICATION

This application is a continuation-in-part of application Ser. No. 08/532,963; filed Sep. 25, 1995 now U.S. Pat. No. 5,759,149, the specification of which is expressly incorporated herein by reference.

BACKGROUND AND SUMMARY OF THE INVENTION

The present invention relates to patient-support devices, and particularly, to infant thermal support devices of the type having a humidity controlled environment for a patient supported by the device. More particularly, the present invention relates to a self-contained humidifier module that is inserted into a patient-support apparatus.

It is conventional to humidify the air which is circulated inside an infant incubator. Conventional incubators, or patient thermal support devices as they are known, have systems for recirculating warmed air in the environment in which the infant resides. The environment may be enclosed by some type of housing or canopy over a support or the environment may be a space which is controlled by one or more curtains of heated air. The objective is to provide controlled humidity in the environment by adding moisture to the heated air. It is desirable to humidify the air so that evaporative heat losses from a patient exposed to the humidified air are minimized. See, for example, U.S. Pat. Nos. 5,224,923 and 5,336,156 showing humidifiers associated with infant incubators.

The present invention is a humidifier module for a patient-support apparatus including an opening into which the module is inserted, an electrical service connector, an air inlet port, and an air outlet port. The humidifier module, which is to be inserted into the patient-support apparatus, comprises a water reservoir for holding water, a heater for heating the water, an air chamber with an air inlet port and an air exhaust port for mating with the air inlet and outlet ports of the support apparatus, and an electrical connector for mating with the electrical service connector of the patient-support apparatus. The patient-support apparatus is provided with a humidified environment for the patient when the humidifier module is inserted into the opening of the patient-support apparatus.

The patient-support apparatus may include one or more external doors that normally close the opening of the patient-support apparatus. The external doors are opened by the insertion of the humidifier module through the opening of the patient support apparatus. The patient-support apparatus may also include one or more internal doors that normally close the air inlet and outlet ports of the patient-support apparatus. The internal doors are opened by the insertion of the humidifier module through the opening and into the patient-support apparatus.

The humidifier module may include one or more spill damper doors that close the air inlet port and air exhaust port of the humidifier module to prevent hot water heated by the heater from spilling out of the humidifier module when the humidifier module is removed from the patient-support apparatus. The patient-support apparatus may include door opener tabs that engage and open the spill damper doors when the humidifier module is inserted into the patient-support apparatus. In preferred embodiments, the humidifier module includes a pair of door openers that are positioned beneath the respective air inlet and exhaust ports and each door opener is formed to include a recess that catches any water that inadvertently spills out of the humidifier module through the air inlet and exhaust ports.

In the preferred embodiments, a substantial portion of each of the water reservoir, the heater, and the air chamber pass through the opening of the patient-support apparatus as the humidifier module is inserted into the apparatus. The humidifier module can include a refill door that is positioned to lie outside a compartment of the patient-support apparatus in which the humidifier module is received. The refill door can be opened so that water can be poured into the water reservoir without having to remove the humidifier module from the patient-support apparatus.

It will be appreciated, therefore, that the patient-support apparatus of the present invention comprises a compartment for accepting a removable self-contained humidifier module, an air inlet in fluid communication with the compartment, an air outlet in fluid communication with the compartment, and an electrical service connector positioned to lie in the compartment. The humidifier module includes a water heater chamber and cooperating inlets and outlets for connecting with the air inlets and outlets of the patient-support when the humidifier module is inserted into the compartment. The humidifier module further includes an electrical connector that couples to the electrical service connector of the patient-support apparatus and a heater coupled to the electrical connector. In preferred embodiments, the electrical connector of the humidifier module aligns with and automatically connects to the electrical service connector of the patient-support apparatus when the humidifier module is inserted into the patient-support apparatus.

Thus, there is provided a patient-support apparatus having a patient support and a fluid circulation system with a flow path that directs circulated fluid through the patient support to provide a thermally controlled environment for a patient. The patient support includes a compartment for accepting a removable self-contained humidifier module, an inlet port in fluid communication with the compartment and an outlet port in fluid communication with the compartment. The apparatus also includes a first door pivotably coupled to the patient support and normally closing the inlet port, a second door pivotably coupled to the patient support and normally closing the outlet port. The humidifier module includes a water container for containing water, an inlet port for connecting with the outlet port of the patient-support when the humidifier module is inserted into the compartment, an exhaust port for connecting with the inlet port of the patient-support when the humidifier module is inserted into the compartment, and first and second door openers arranged to engage and pivot the respective first and second doors to an open position to allow at least some to the fluid in the first path to be diverted through the humidifier module and over the water contained in the water container.

The preferred humidifier module of the present invention comprises a container for holding water and an air chamber above the water. The container may have an air inlet port and an air exhaust port providing for air flow movement through the chamber. The humidifier module includes a heater for heating the water and a water reservoir for holding additional water. The humidifier further includes a control valve coupled to the water reservoir and coupled to the container. The control valve has a closed configuration blocking the flow of water from the water reservoir to the container and the control valve has an opened configuration allowing the flow of water from the water reservoir to the container. A level sensor senses the water level in the container and provides a signal to the control valve to move the control valve between the opened and closed configurations.

For safety reasons, the preferred humidifier module comprises a locking mechanism that locks the humidifier module to the patient support of the patient-support apparatus when a temperature sensor, which is coupled to the locking mechanism, senses a temperature that exceeds a predetermined temperature. The locking mechanism includes a locking post and a solenoid that extends the locking post to a locking position and that retracts the locking post to a releasing position depending upon the temperature sensed by the temperature sensor. The patient-support apparatus is formed to include an aperture that receives the locking post when the locking post extends to the locking position.

In accordance with present invention, the patient-support apparatus comprises a patient support having a first chamber, a second chamber and a fluid-flow orifice between the first and second chambers. A fan is positioned to lie in the first chamber. The fan is operable to move fluid through the orifice into the second chamber. A laminar flow profile structure is appended to the patient support in the second chamber and configured to maintain laminar flow of the fluid as the fluid enters the second chamber from the first chamber. The patient support is formed to include at least one flow aperture in fluid communication with the second chamber and the fluid flows from the second chamber through the aperture to an area surrounding a patient supported on the patient support.

In preferred embodiments, the patient support includes a platform tub and a platform cover positioned to lie above a channel formed in the platform tub. The platform cover is formed to include a mattress-receiving aperture and a plurality of vent slots that are arranged around the mattress-receiving aperture. The vent slots are in fluid communication with the channel so that some of the fluid flowing in the channel passes upwardly through each of the vent slots. The patient support further includes a bottom wall having a datum surface in the first chamber and inclined surfaces in the channel. The inclined surfaces are configured so that air exits each vent slot of the platform cover at substantially the same velocity.

Additional features and advantages of the invention will become apparent to those skilled in the art upon consideration of the following detailed description of a preferred embodiment exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
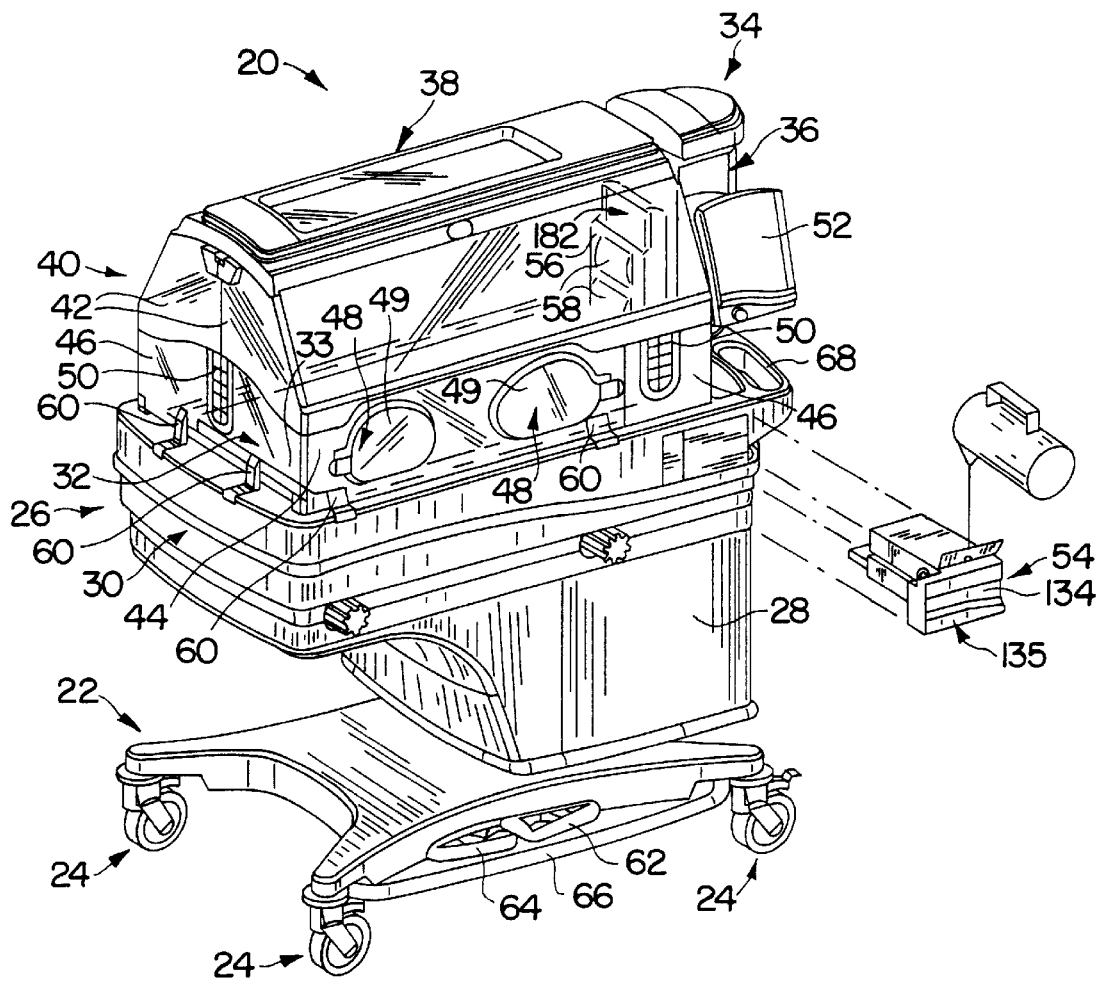
FIG. 1 is a perspective view of a patient-support apparatus according to the present invention showing a base, a patient support carried above the base, a humidifier module beside the patient support being filled with water, and an isolation chamber enclosed by an overlying canopy, a pair of transparent side guard panels, and a pair of transparent end guard panels.

A thermal support apparatus or patient-support apparatus 20, such as an infant warming device or incubator, includes a base 22, a plurality of castors 24 extending downwardly from base 22, and an infant supporting portion or patient support 26 supported above base 22 as shown in FIG. 1. Patient support 26 includes a pedestal 28 coupled to base 22 for vertical movement, a platform tub 30 supported by pedestal 28, and a mattress 32 supported on platform tub 30. Mattress 32 has an upwardly facing patient-support surface 33. Patient-support apparatus 20 also includes a canopy support arm 34 including a telescoping vertical arm 36 and a horizontal overhead arm 38. A canopy 40 is coupled to overhead arm 38 and is positioned to lie above platform tub 30. Canopy 40 includes a pair of canopy halves 42 coupled to overhead arm 38 for pivoting movement between a lowered position shown in FIG. 1 and a raised position (not shown).

A pair of transparent side guard panels 44 and a pair of transparent end guard panels 46 extend upwardly from platform tub 30 as shown in FIG. 1. Side guard panels 44 and end guard panels 46 cooperate with canopy halves 42 and overhead arm 38 to provide patient-support apparatus 20 with an isolation chamber. Side guard panels 44 may be formed to include a pair of access ports that are normally closed by access door assemblies 48. Access door assemblies 48 include door panels 49 that can be opened to allow access to a patient, such as an infant, supported by thermal support apparatus 20 within the isolation chamber. Each end guard panel 46 is formed to include at least one U-shaped window and a pass-through grommet 50 is positioned to lie in each U-shaped window. Wires and tubes (not shown) can be routed into the isolation chamber through pass-through grommets 50.

Patient-support apparatus 20 includes a user interface panel 52 for monitoring various systems that control the temperature and humidity of the isolation chamber and for allowing caregivers to input various control parameters into memory of a control system of patient-support apparatus 20. Patient-support apparatus 20 also includes a humidifier module 54 that can be filled with water and inserted into platform tub 30. Heated air is blown through humidifier module 54 and directed into the isolation chamber. A tower 56 is positioned to lie in the isolation chamber. Tower 56 supports various sensors 58, such as patient environmental sensors and noise and light sensors, and also provides a return-air path for the air being circulated through the isolation chamber.

Hinges 60 are provided so that side guard panels 44 and the end guard panel 46 at a foot end of patient support 26 can pivot downwardly away from canopy 40 to provide increased access to the infant supported by patient-support apparatus 20. Up and down buttons (not shown) can be pressed to extend and retract vertical arm 36 of canopy support arm 34, thereby raising and lowering, respectively, overhead arm 38 and canopy 40. Patient-support apparatus 20 includes an up pedal 62 that can be depressed to raise patient support 26 relative to base 22 and a down pedal 64 that can be depressed to lower patient support 26 relative to base 22. Patient-support apparatus 20 also includes a side bumper 66 that protects pedals 62, 64 and other components, such as base 22 and pedestal 28, from inadvertent impact. Platform tub 30 is formed to include a handle 68 on each side of canopy support arm 34. Handles 68 can be grasped by a caregiver to maneuver patient-support apparatus 20 during transport.

Other features of patient-support apparatus 20 are discussed in detail in co-pending applications Ser. No. 08/925,981; Ser. No. 08/925,873; Ser. No. 08/926,380; and Ser. No. 08/926,381 filed concurrently herewith, all of which are incorporated herein by reference.

Figure 2:
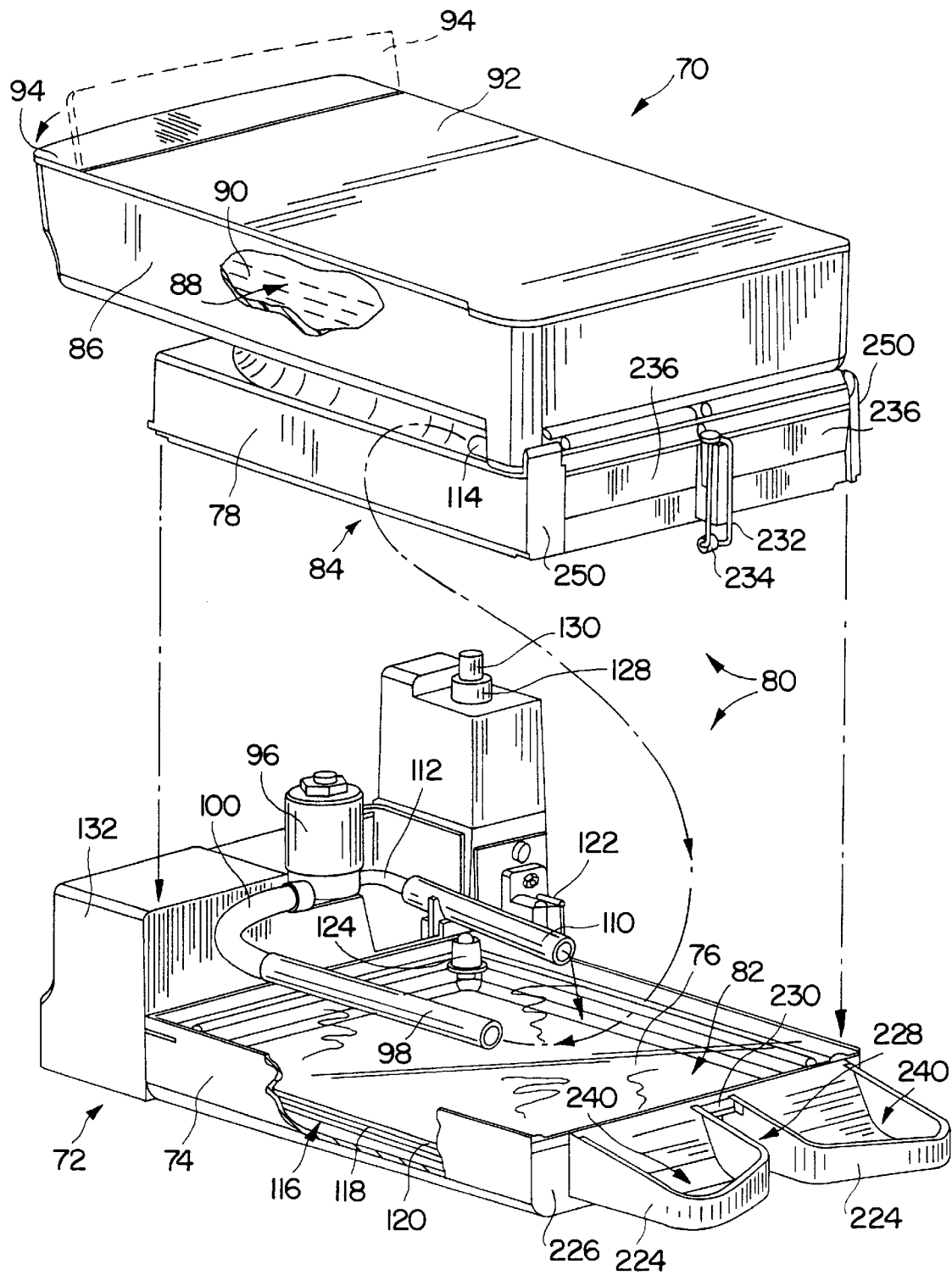
FIG. 2 is a perspective view of the humidifier module of FIG. 1 showing a lower water heater portion of the humidifier module and an upper water reservoir portion of the humidifier module.

Patient-support apparatus 20 includes humidifier module 54 as previously described. Humidifier module 54 includes an upper reservoir portion 70 and a lower 30 water heater portion 72 as shown in FIG. 2. Heater portion 72 includes a container bottom 74 configured to hold water 76. Reservoir portion 70 includes a container top 78 that seats against container bottom 74 to provide humidifier module 54 with a chamber 80. Receipt of water 76 in container bottom 74 subdivides chamber 80 into a water-filled portion 82 and an air-filled portion 84. Reservoir portion 70 includes a water reservoir container 86 positioned to lie above container top 78. Container 86 has a chamber 88 in which additional water 90 is stored.

Humidifier module 54 includes a reservoir cover 92 fixed to reservoir container 86 above chamber 88 as shown in FIG. 2. A refill door 94 pivotably couples to reservoir container 86 adjacent to an edge of cover 92. Refill door 94 is movable relative to container 86 between a closed position, shown in FIG. 2 (in solid), and an opened position, shown in FIG. 2 (in phantom). When refill door 94 is in the opened position, water can be poured into chamber 88 of reservoir container 86 as shown in FIG. 1. Refill door 94 can be moved between the opened and closed positions when humidifier module 54 is separated away from platform tub 30 and when humidifier module 54 is installed in platform tub 30. Thus, when humidifier module 54 is installed in platform tub 30, water reservoir container 86 can be filled with water 88 without having to remove humidifier module 54 from platform tub 30.

Humidifier module 54 includes a control valve 96, shown in FIG. 2, that controls the flow of water from reservoir container 86 to container bottom 74. An inlet tube 98 is coupled to flow control valve 96 by an inlet connector 100 and an outlet tube 110 is coupled to flow control valve 96 by an outlet connector 112. Container 86 includes a water outlet 114 in fluid communication with chamber 88. Inlet tube 98 is coupled to water outlet 114 so that a portion of additional water 88 flows from container 86 through water outlet 114, inlet tube 98, and inlet connector 100 to control valve 96. Control valve 96 is actuatable between a closed configuration in which additional water 88 is blocked from flowing into container bottom 74 and an opened configuration in which additional water 88 flows into container bottom 74 to thereby, become water 76.

Figure 5:
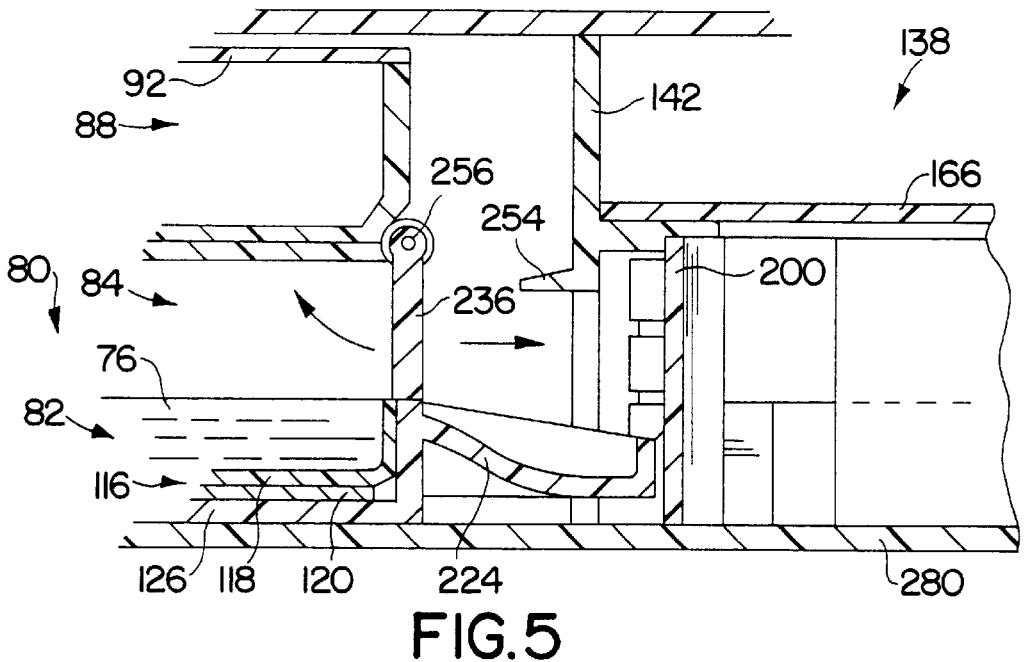
FIG. 5 is a sectional view taken along line 5—5 of FIG. 4.
Figure 7:
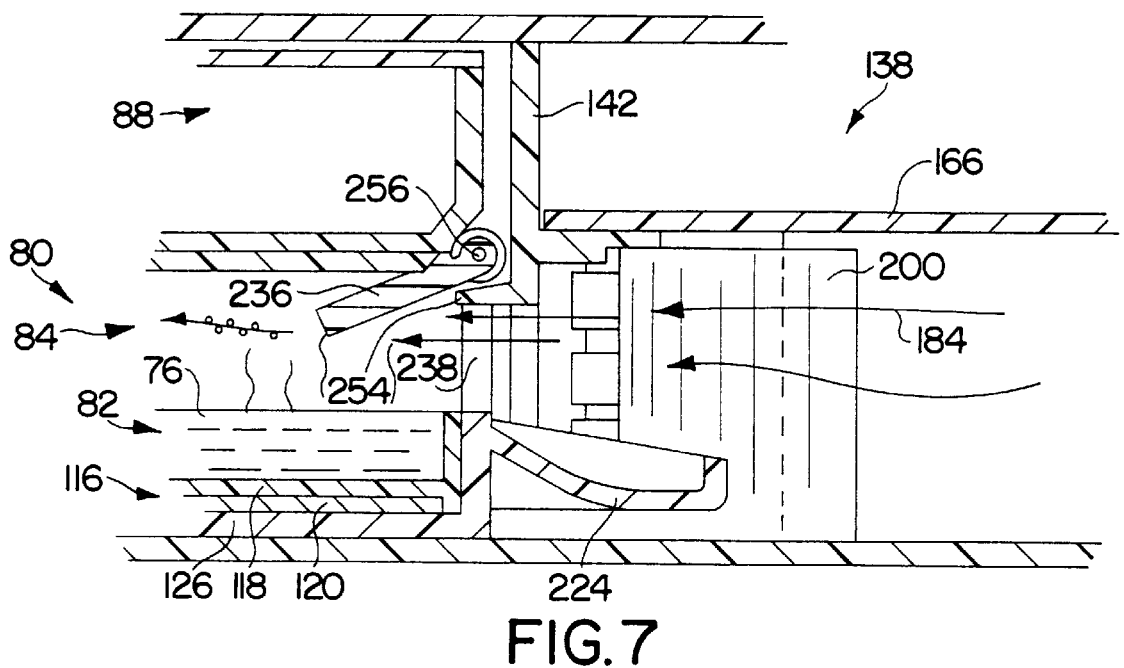
FIG. 7 is a sectional view taken along line 7—7 of FIG. 6 showing one of a pair of spill-damper doors of the humidifier module pivoted to an upward position by a respective door opener tab projecting from a wall of the patient support to allow air to enter the humidifier module above heated water contained in the humidifier module.

Humidifier module 54 includes a heater 116 having a heater pan 118 and a heater pad 120 as shown in FIGS. 2, 5, and 7. Humidifier module 54 also includes an electrical connector 122, a portion of which is electrically coupled to heater pad 120. Power is supplied to heater pad 120 through electrical connector 122 so that water 76 in water-filled portion 82 of chamber 80 is heated and evaporated into air-filled portion 84 of chamber 80. As water 76 is heated and evaporated, the amount of water 76 in container bottom 74 decreases.

Humidifier module 54 includes a water level sensor 124, shown in FIG. 2, that is operatively connected to control valve 96. When the level of water 76 in container bottom 74 drops to a predetermined level, sensor 124 provides a signal that switches control valve 96 from the closed configuration to the opened configuration so that water 88 from water reservoir container 86 flows through control valve 96 into container bottom 74 as previously described. When the level of water 76 rises to a predetermined level, sensor 124 provides a signal that switches control valve 96 from the opened configuration back to the closed configuration so that water 88 is prevented from flowing through control valve 96 into container bottom 74. In a preferred embodiment, sensor 124 is a commercially available Honeywell Model No. LL 105000 liquid level sensor.

Heater pad 120 is sandwiched between heater pan 118 and a bottom wall 126 of container bottom 74 as shown best in FIGS. 5 and 7. As heater pad 120 heats water 76, bottom wall 126 is also heated. Humidifier module 54 includes a locking solenoid 128, shown in FIG. 2, and a temperature sensor (not shown) that is operatively coupled to locking solenoid 128. The temperature sensor is positioned to lie between heater pan 118 and heater pad 120 and the temperature sensed by the temperature sensor is correlated to the temperature of bottom wall 126. When the temperature sensed by the temperature sensor exceeds a threshold level, the temperature sensor provides a signal to locking solenoid 128 to extend a locking pin 130 of locking solenoid 128 to a locking position. When the temperature sensed by the temperature sensor is below the threshold level, the temperature sensor provides a signal to locking solenoid 128 to retract locking pin 130 to a releasing position.

Lower water heater portion 72 includes a circuit housing 132 and an electric circuit (not shown) that is contained in an internal compartment of circuit housing 132. Control valve 96, heater 116, electrical connector 122, water level sensor 124, and locking solenoid 128 are all coupled to the electric circuit contained in circuit housing 132. The electric circuit includes serial port interface circuitry for sending data to and receiving data from a main control circuit of patient-support apparatus 20. The electric circuit also includes analog-to-digital conversion circuitry, temperature conditioning circuitry, water fill logic circuitry, humidifier lock-in logic circuitry, temperature lock out comparator circuitry, pan temperature comparator circuitry, humidifier identification code and status circuitry, and voltage regulator circuitry for monitoring and supplying an appropriate level of power to the various components of the electric circuit.

Heater pad 120 is operated by 120 V AC power and the electric circuit includes both heater control circuitry and optical isolation circuitry that isolates the majority of the electric circuit from the 120 V AC power. The electric circuit also includes a set of status LED's, indicated generally by reference numeral 134 shown in FIG. 1. Status LED's 134 include a "humidifier connect" LED that, when lit, indicates that humidifier module 54 is connected and receiving power; a low water LED that, when lit, indicates that there is no additional water 88 in water reservoir container 86 and that the level of water 76 is below a predetermined threshold level; and a "lock" LED that, when lit, indicates that locking pin 130 of locking solenoid 128 is in the locking position.

Figure 3:
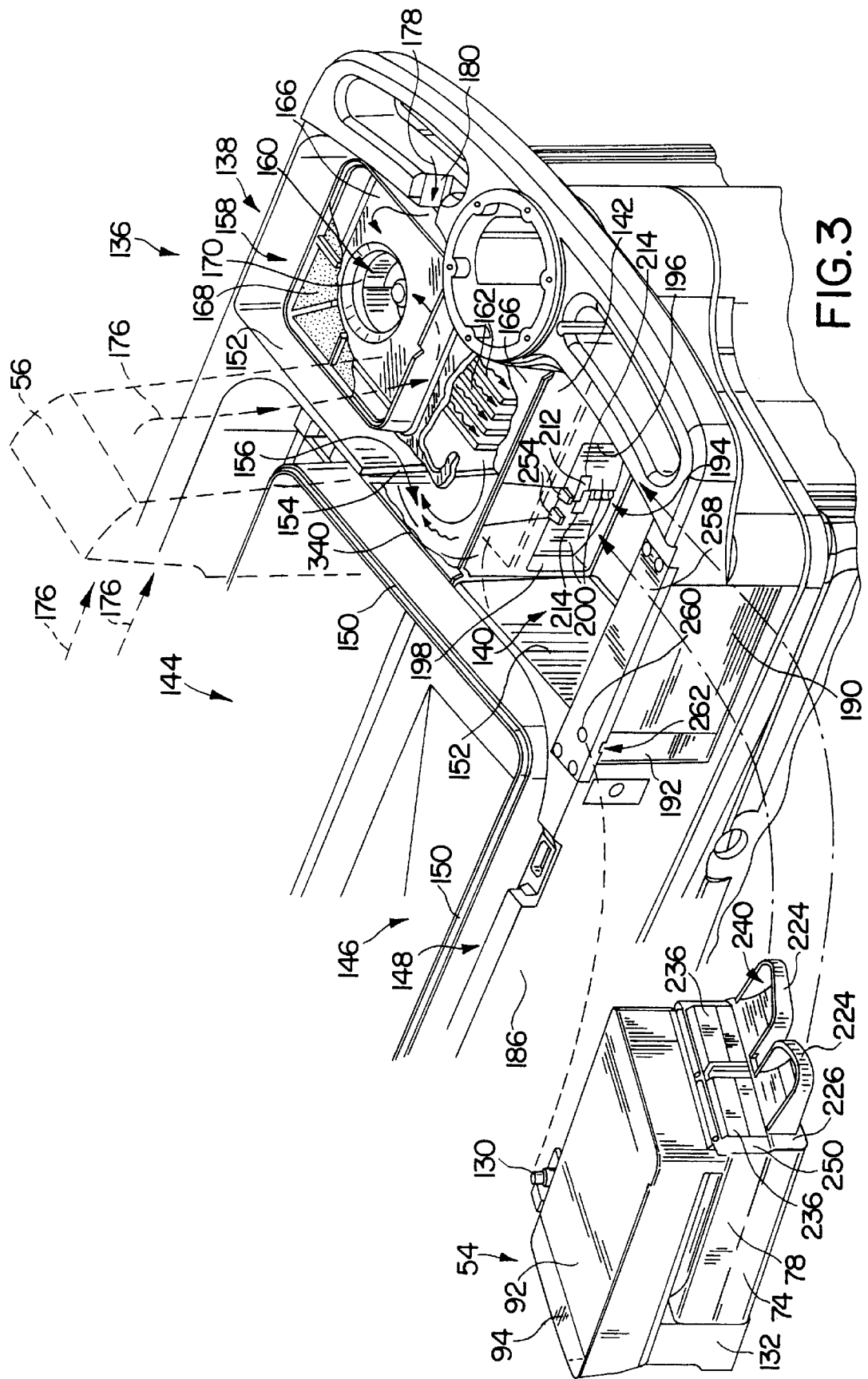
FIG. 3 is a perspective view of the patient-support apparatus of FIG. 1 showing various components of an air circulation system situated in a first internal compartment of the patient support and showing a path by which the humidifier module can be inserted into a second internal compartment of the patient support adjacent to the first internal compartment.

Humidifier module 54 includes a handle recess 135, shown in FIG. 1, for use by a caregiver to selectively insert humidifier module 54 into and remove humidifier module 54 from platform tub 30 as previously described. Platform tub 30 includes a first chamber 136 that is subdivided into a first internal compartment 138 and a second internal compartment 140 by a partition wall 142 as shown in FIG. 3. Platform tub 30 also includes a second chamber 144 that is subdivided into a mattress well 146 and an air flow channel 148 by a set of internal walls 150. First chamber 136 is separated from second chamber 144 by a pair of transversely extending bulkhead walls 152. Walls 152 are spaced-apart so that inner edges 154 of walls 152 define an opening 156 between first chamber 136 and second chamber 144.

Patient-support apparatus 20 includes an air or fluid circulation system 158 that circulates air from chamber 136, through opening 156, and into air flow channel 148 as shown in FIG. 3. Air circulation system 158 includes a fan 160 and a plurality of heat transfer fins 162 as shown in FIG. 3. Fan 160 includes a disk 163, shown in FIG. 9, with a plurality of upwardly extending fan blades 164 appended thereto and a motor (not shown) that is operated to rotate disk 163 and fan blades 164. Air circulation system 158 includes a divider or top plate 166 positioned to lie above fan 160 and an air filter 168 positioned to lie above top plate 166 as shown in FIG. 3. Top plate 166 divides first internal compartment 138 into an upper air mixing space and a lower air make-up space and top plate 166 is formed to include a fan inlet aperture 170. Platform tub 30 includes a cylindrical wall 172, shown in FIGS. 4 and 6, that substantially surrounds fan blades 164. Cylindrical wall 172 is formed to include a fan outlet port 174.

Rotation of fan blades 164 by the motor of fan 160 causes air to be drawn downwardly from the air mixing space through air filter 168 and fan inlet aperture 170 of top plate 166 and into the air make-up space occupied by fan blades 164. The air drawn downwardly by fan blades 164 is a mixture of both circulated air, indicated by arrows 176 shown in FIG. 3 (in phantom), and ambient room air, indicated by arrows 178. Ambient room air 178 enters internal compartment 138 of platform tub 30 through an air inlet port 180 formed in platform tub 30 adjacent to one of handles 68. Circulated air 176 is pulled from the isolation chamber above patient support 26 through a vent opening 182, shown in FIG. 1, formed in tower 56 and then is directed downwardly through an interior region of tower 56 into internal compartment 138 as shown in FIG. 3.

Figure 4:
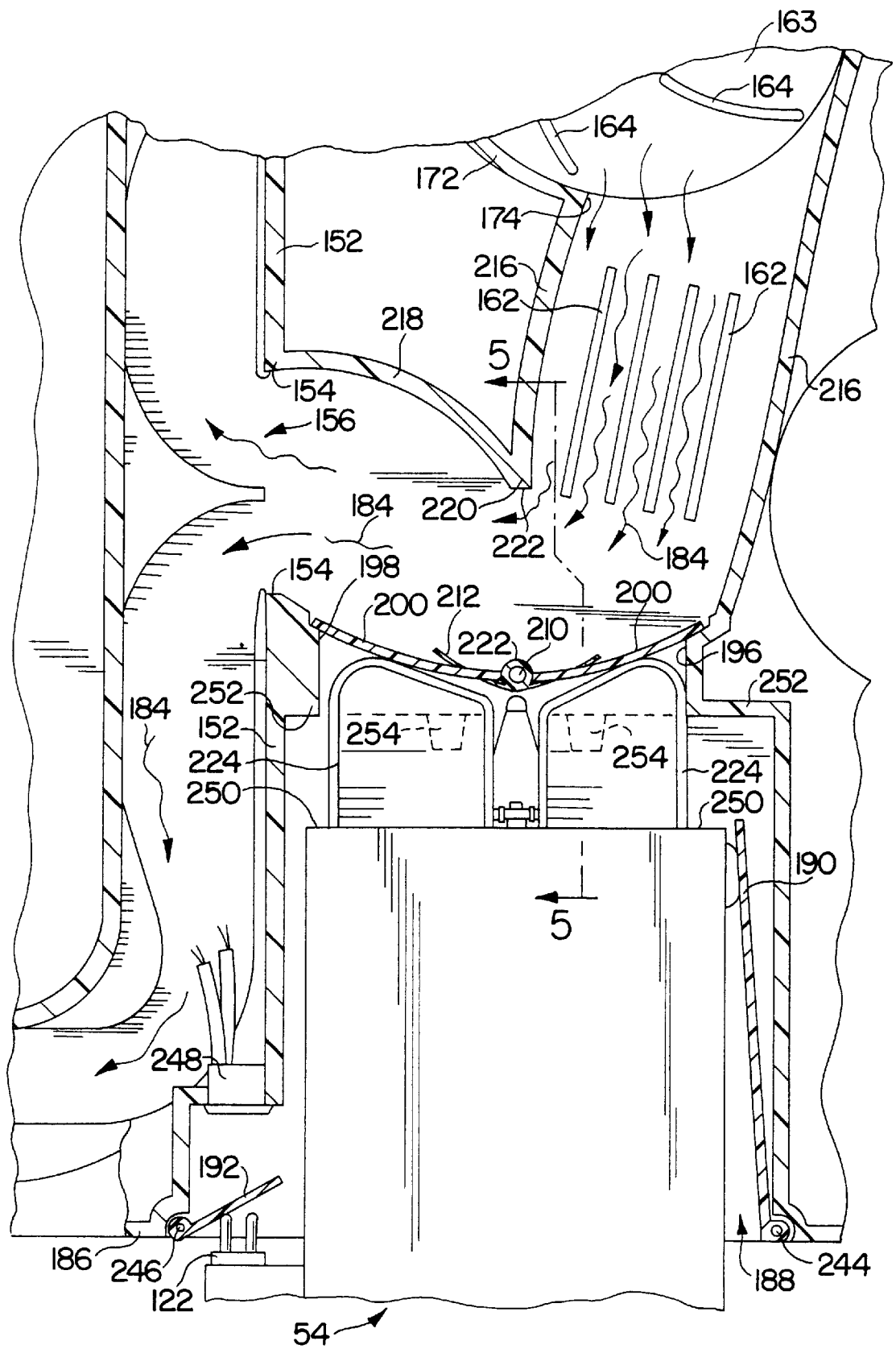
FIG. 4 is an enlarged top plan view of the patient-support apparatus of FIG. 3, with portions broken away, showing the humidifier module partially inserted into the second internal compartment of the patient support, external doors of the patient support in a partially opened position due to the partial insertion of the humidifier module, internal doors of the patient support in a closed position blocking air from moving from the first internal compartment into the second internal compartment, and a pair of door openers of the humidifier module contacting the internal doors of the patient support.

Rotation of fan blades 164 forces the mixture of air 176, 178 through fan outlet port 174 and across heat transfer fins 162 as shown, for example, in FIG. 4. Air circulation system 158 includes a heater (not shown) that supplies heat to heat transfer fins 162 so that, as the air moves across heat transfer fins 162, the air is warmed to provide a stream of heated air 184. The main control circuit of patient-support apparatus 20 includes circuitry for monitoring the temperature in the isolation chamber, circuitry for sensing air flow, circuitry for sensing the rotational speed of fan 160, circuitry for controlling the rotational speed of fan 160, and circuitry for controlling the amount of heat supplied from the heater to heat transfer fins 162. The main control circuit is a microprocessor-based circuit having computer software that controls the operation of the various systems of patient-support apparatus including air circulation system 158. Thus, the main control circuit controls the temperature in the isolation chamber by controlling the temperature of heated air 184.

Figure 6:
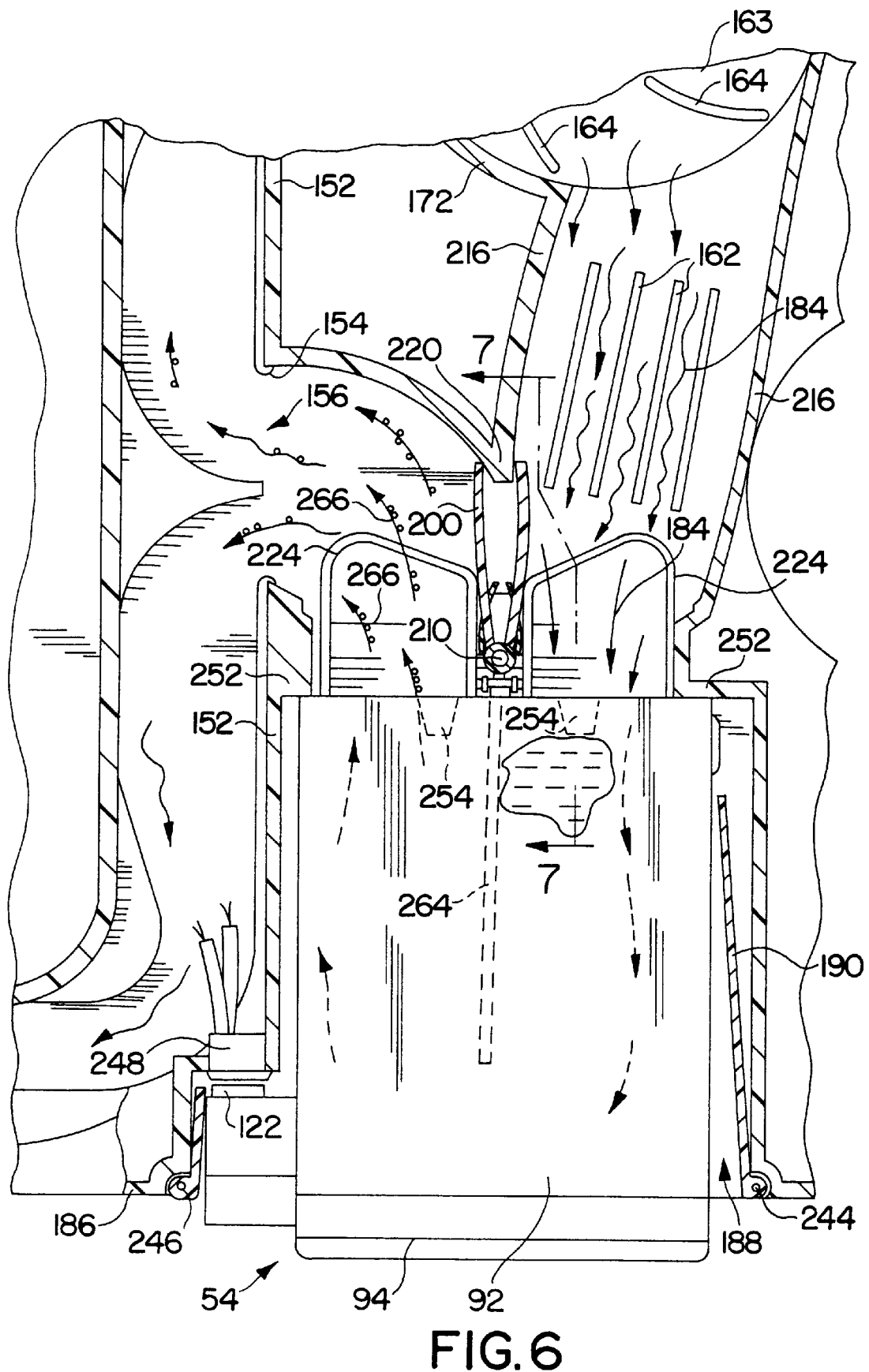
FIG. 6 is an enlarged top plan view similar to FIG. 4 after the humidifier module is fully inserted into the second internal compartment of the patient support showing the door openers of the humidifier module operating to hold the internal doors of the patient support in an opened position to allow circulation of air from the first compartment into the humidifier module situated in the second compartment.

Platform tub 30 includes an outer wall 186 that is formed to include an opening 188 as shown in FIGS. 4 and 6. Humidifier module 54 is inserted into compartment 140 through opening 188. Patient-support apparatus 20 includes a first external door 190 and a second external door 192, each of which are spring-biased to a position closing respective portions of opening 188 when humidifier module 54 is removed from compartment 140 as shown in FIGS. 1 and 3. Partition wall 142 is formed to include an opening 194, part of which provides an air outlet port 196 between first internal compartment 138 and second internal compartment 140 and part of which provides an air inlet port 198 between first internal compartment 138 and second internal compartment 140 as shown in FIG. 3. Patient-support apparatus 20 includes a pair of internal doors 200, one of which normally closes air outlet port 196 and the other of which normally closes air inlet port 198. Internal doors 200 are each coupled to a vertically extending pivot pin 210 as shown in FIGS. 4 and 6. A torsion spring 212 is also coupled to pivot pin 210 and each door 200 includes a slot 214 that receives a respective end of torsion spring 212. Torsion spring 212 biases each door 200 to a respective closed position as shown in FIG. 4.

When doors 200 are closed, as shown in FIGS. 3 and 4, heated air 184 flows through first internal compartment 138 and into air flow channel 148 without entering second internal compartment 140. Heat transfer fins 162 are positioned to lie between a pair of first stage walls 216 of platform tub 30 as shown in FIG. 4. Fins 162 and walls 216 are oriented so that air 176, 178 being forced by fan 160 through fan outlet port 174 is directed toward the door 200 that closes air outlet port 196 as shown in FIG. 4. Platform tub 30 includes a second stage wall 218 integrally formed with one of first stage walls 216 to provide platform tub 30 with a corner or wall portion 220. Wall portion 220 is transversely spaced apart from pivot pin 210 to define an orifice 222 therebetween. Doors 200 are curved so that heated air 184 is circulated from the path defined by heat transfer fins 162 and walls 216, through orifice 222, and into a path defined between the door 200 that closes air inlet port 198 and second stage wall 218. Fan 160 further circulates heated air 184 from first internal compartment 138, through opening 156 between edges 154 of walls 152, and into air flow channel 148.

Humidifier module 54 includes a pair of door openers 224 that are appended to a back wall 226 of container bottom 74 as shown, for example, in FIGS. 2 and 3. Door openers 224 are spaced apart to define a pin-receiving space 228 therebetween. A catch ledge 230 extends between door openers 224 adjacent to back wall 226 of container bottom 74. Humidifier module 54 includes a latch spring 232 coupled to upper water reservoir portion 70. Latch spring 232 includes a bottom catch portion 234 that catches on catch ledge 230 to help secure upper water reservoir portion 70 to lower water heater portion 72.

Reservoir portion 70 of humidifier module 54 includes a pair of spill damper doors 236, one of which covers an air inlet port 238 of container top 78, shown in FIG. 7, and the other of which covers an air exhaust port (not shown) of container top 78 that is similar to air inlet port 238. Each door opener 224 is formed to include a recess 240 for catching water that inadvertently spills out of container bottom 74 between spill damper doors 236 and respective back wall 226 of container bottom 74 during insertion and removal of humidifier module 54 relative to platform tub 30.

When humidifier module 54 is inserted through opening 188 into compartment 140 of platform tub 30, door openers 224 engage first external door 190 to pivot door 190 about a pivot pin 244, shown in FIGS. 4 and 6, from the closed position to an opened position. In addition, electrical connector 122 engages second external door 192 to pivot door 192 about a pivot pin 246 from the closed position to an opened position. Patient-support apparatus 20 includes an electrical service connector 248 that is coupled to the main control circuit of patient-support apparatus 20. Electrical connector 122 of humidifier module 54 is aligned with and automatically connects to electrical service connector 248 when humidifier module 54 is fully inserted into compartment 140 as shown in FIG. 6.

As humidifier module 54 is inserted into compartment 140, door openers 224 engage respective internal doors 200, as shown in FIG. 4, and pivot doors 200 from their respective closed positions to respective opened positions as shown in FIG. 6. When humidifier module 54 is fully inserted into compartment 140, pivot pin 210 is received in pin-receiving space 228 between door openers 224. In addition, door openers 224 hold doors 200 in their opened positions so that distal ends of doors 200 engage wall portion 220 to close orifice 222. When humidifier module 54 is fully inserted into compartment 140, outer portions of back wall 226 of container bottom 74 and stop portions 250 of container top 78, shown in FIGS. 2 and 3, engage respective stop walls 252 of platform tub 30 to prevent insertion of humidifier module 54 past the position shown in FIG. 6.

A pair of door opener tabs 254 are appended to partition wall 142 above opening 194 and extend therefrom into compartment 140 as shown in FIG. 3. One of door opener tabs 254 is positioned to lie over air outlet port 196 and the other of door opener tabs 254 is positioned to lie over air inlet port 198. A top portion of each spill damper door 236 is mounted to container top 78 by a horizontal pivot pin 256 as shown in FIGS. 5 and 7. When humidifier module 54 is inserted into compartment 140, tabs 254 engage respective spill damper doors 236 to pivot doors 236 upwardly about respective pivot pins 256 from respective closed positions, shown in FIGS. 2, 3, and 5, to respective opened positions, as shown in FIG. 7.

Thus, when humidifier module 54 is fully inserted into platform tub 30, a portion of each door opener 224 is positioned to lie in first internal compartment 138 to hold each respective door 200 in the opened position and a portion of each door opener tab 254 is positioned to lie in chamber 80 to hold each respective spill damper door 236 in the opened position. In addition, air outlet port 196 of transition wall 142 is adjacent to and mates with air inlet port 238 of humidifier module 54 and air inlet port 198 of transition wall 142 is adjacent to and mates with the air exhaust port of humidifier module 54 when humidifier module 54 is fully inserted into platform tub 30.

Platform tub 30 includes a top bar 258 that extends across the top boundary of opening 188 formed in outer wall 186 of platform tub 30 as shown in FIG. 3. Top bar 258 is formed to include an aperture 260 and an entry notch 262 that extends from the front edge of top bar 258 to aperture 260. When humidifier module 54 is inserted through opening 188 into compartment 140 of platform tub 30, locking pin 130 is in the releasing position retracted into locking solenoid 128 and a top portion of locking pin 130 moves through entry notch 262 into alignment with aperture 260. When locking solenoid 128 actuates locking pin 130 from the releasing position to the locking position, due to the heating of bottom wall 126 of container bottom 74 by heater pad 120 as previously described, locking pin 130 moves upwardly into aperture 260. Receipt of locking pin 130 in aperture 260 locks humidifier 54 in compartment 140 of platform tub 30 and prevents the removal of humidifier module 54 from platform tub 30 until locking solenoid 128 retracts locking pin 130 out of aperture 260 to the releasing position.

While humidifier module 54 is fully inserted into platform tub 30 so that doors 200 are in the opened positions, as shown in FIGS. 6 and 7, heated air 184 flows from first internal compartment 138 through both air outlet port 196 of partition wall 142 and air inlet port 238 of humidifier module 54 into air-filled portion 84 of chamber 80. Heat transfer fins 162 and first stage walls 216 are oriented to direct heated air 184 substantially straight into humidifier module 54 as shown in FIG. 6. Container top 78 includes a vertical wall 264, shown in FIG. 6 (in phantom), that partitions air-filled portion 84 of chamber 80 into an air in-flow side and an air out-flow side. Heated air 184 flows around vertical wall 264 and then out of humidifier module 54 and back into first internal compartment 138 through both the air exhaust port of humidifier module 54 and air inlet port 198 of partition wall 142.

As heated air 184 flows through chamber 80 of humidifier module 54, heated air 184 picks up moisture due to the evaporation of water 76 into chamber 80, as previously described. Thus, heated air 184 is transformed into heated and humidified air 266 while passing through humidifier module 54 as shown in FIG. 6. Heated and humidified air 266 exits humidifier module 54 along the out-flow path defined by vertical wall 264 of container top 78 and is directed toward second stage wall 218 of platform tub 30. Second stage wall 218 is curved to redirect heated and humidified air 266 from first internal compartment 138, through opening 156 between edges 154 of walls 152, and into air flow channel 148.

Thus, an air fluid stream circulates through platform tub 30 along two different paths depending upon whether humidifier module 54 is inserted into or removed from platform tub 30. When humidifier module 54 is removed from platform tub 30, doors 200 are closed and heated air 184 is circulated from first internal compartment 138 into air flow channel 148 without entering second internal compartment 140. When humidifier module 54 is inserted into second internal compartment 140 of platform tub 30, doors 200 are opened by door openers 224, spill damper doors 236 are opened by door opener tabs 254, and heated air 184 flows through humidifier module 54 to be transformed into heated and humidified air 266 which, in turn, is circulated back into first internal compartment 138 and then into air flow channel 148.

Figure 8:
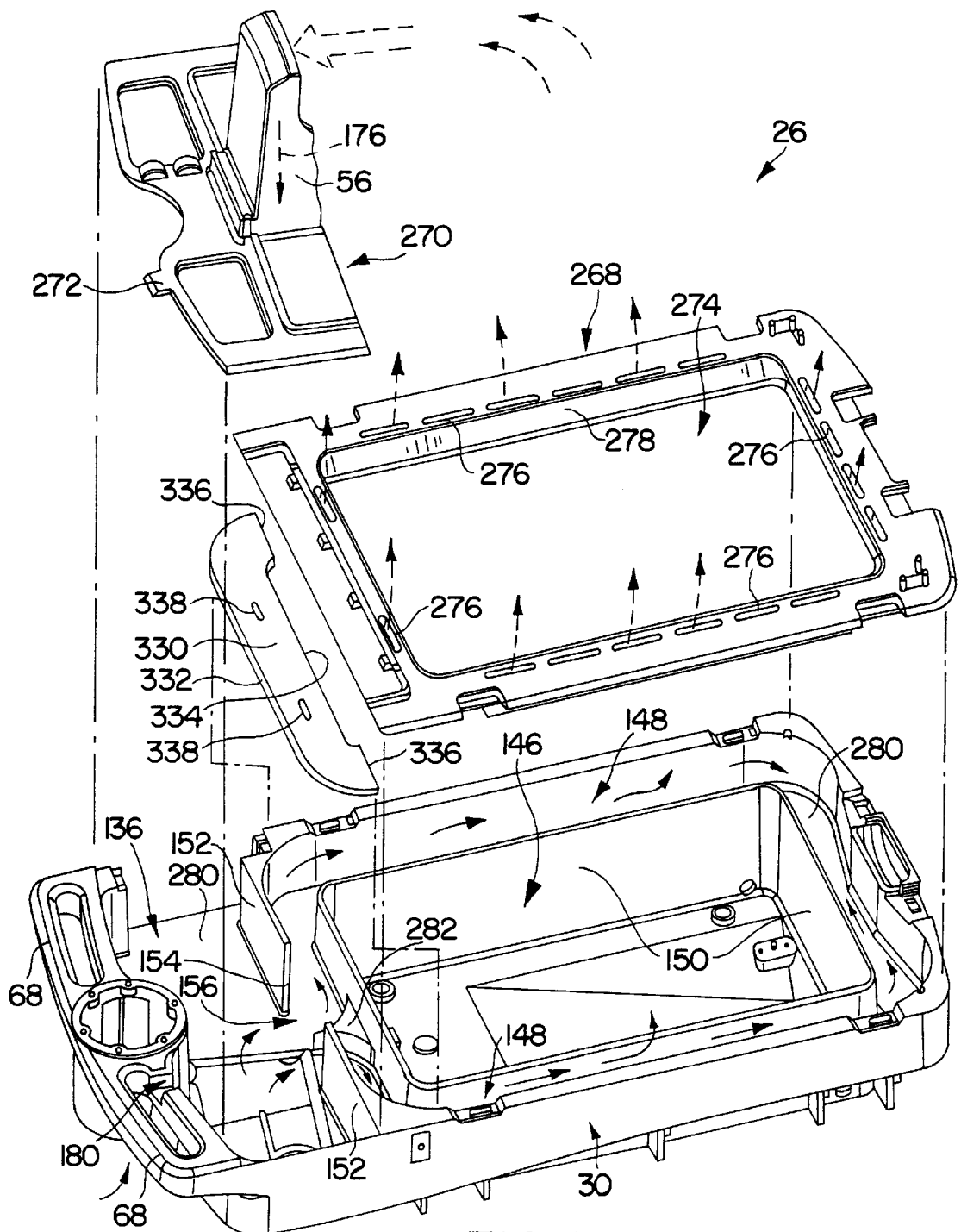
FIG. 8 is an exploded perspective view of the patient support of the patient-support apparatus of FIG. 1 showing the patient support including a platform tub formed with air flow channels, a platform cover formed to include a large rectangular aperture, and a compartment cover formed to include a vertically extending tower.

Patient support 26 includes a platform cover 268 and a compartment cover 270 as shown in FIG. 8. Platform cover 268 couples to platform tub 30 so as to cover air flow channel 148. Compartment cover 270 couples to platform tub 30 so as to cover first and second internal compartments 138, 140. Tower 56 is formed in compartment cover 270. In addition, compartment cover 270 includes a tab 272 that extends over air inlet port 180. Platform cover 268 is formed to include a large rectangular mattress-receiving aperture 274 and a plurality of air vent slots 276 that surround mattress-receiving aperture 272. Platform cover 268 further includes an inner lip 278 that seats against internal walls 150 of platform tub 30.

Platform tub 30 includes a bottom wall 280 to which walls 152 and walls 150 are appended. Platform tub 30 also includes a cover plate 330, shown in FIG. 8, that is positioned to lie in a transverse portion of air flow channel 148 between bottom wall 280 and platform cover 268. Cover plate 330 includes a first edge 332 positioned to lie adjacent to transverse walls 152 of platform tub 30 and a second edge 334 positioned to lie adjacent to the associated transverse wall 150 of platform tub 30. The ends of cover plate 330 are curved and extend from the transverse portion of air flow channel 148 into respective longitudinal portions of air flow channel 148. Patient-support apparatus 20 includes top plate 166, shown in FIGS. 3, 5, and 7, that is positioned to lie in first internal compartment 138 above fan 160 and heat transfer fins 162 as previously described. Cover plate 330 is substantially coplanar with top plate 166 and a portion of edge 332 of cover plate 330 meets an edge (not shown) of top plate 166 at opening 156. The air circulated by fan 160 through fan outlet port 174 passes beneath top plate 166 and through opening 156 into air flow channel 148 beneath cover plate 330.

Cover plate 330 includes end edges 336 extending between first and second edges 332, 334 as shown in FIG. 8. Fan 160 causes air to pass beneath cover plate 330, past end edges 336, and into the longitudinal portions of air flow channel 148. Cover plate 330 is formed to include a pair of bleeder holes 338 which allow some of the air circulating beneath cover plate 330 to move upwardly therethrough into the space above cover plate 330. Some of the air moving upwardly through bleeder holes 328 passes through the air vent slots 276 that are adjacent to tower 56 to provide an air curtain near the head of a patient supported by mattress 32. Patient-support apparatus 20 includes a divider wall 340, shown in FIG. 3, that extends between edges 154 of transverse walls 152 above top plate 166 and cover plate 330 to prevent the air that passes upwardly through bleeder holes 338 from moving back into first internal compartment 138 through opening 156.

Figure 9:
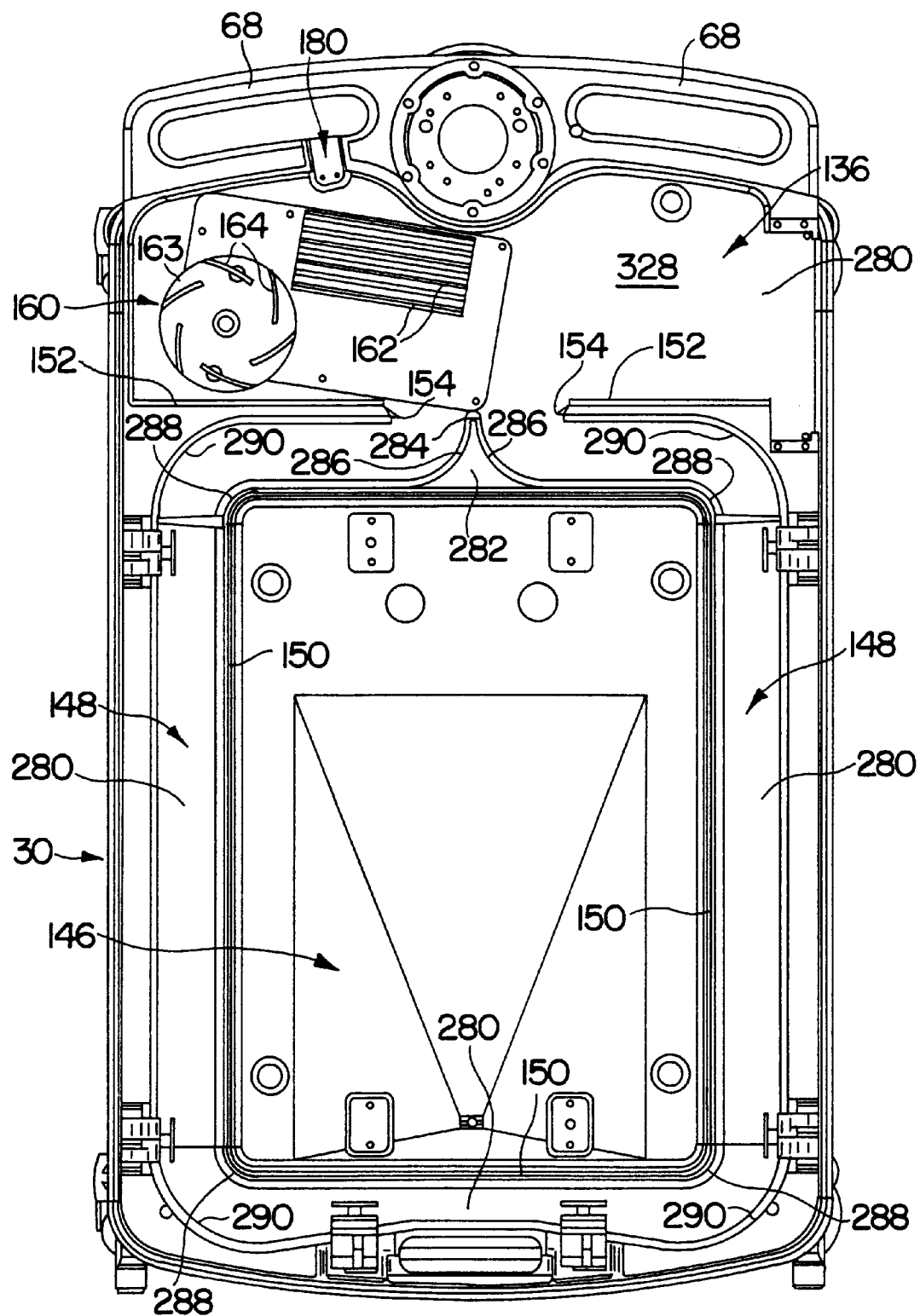
FIG. 9 is a top plan view of the platform tub of FIG. 8 showing the geometry of the air flow channels formed in the platform tub.

A center divider 282 is appended to a bottom surface (not shown) of cover plate 330. Center divider 282 extends downwardly from cover plate 330 and is positioned to lie in the transverse portion of air flow channel 148 between the respective wall 150 and opening 156 as shown in FIGS. 8 and 9. Center divider 282 includes an apex 284 at opening 156 and a pair of curved surfaces 286 extending from apex 284 toward the associated wall 150. Apex 284 cooperates with curved surfaces 286 to split the air passing through opening 156 into two separate air streams which are directed toward opposite sides of platform tub 30. Center divider 282 is configured so that the mass flow rate of air in each air stream is substantially equivalent. Center divider 282 is also configured so that the air passing through opening 156 into air flow channel 148 does not become turbulent.

Internal walls 150 of platform tub 30 are blended together at corners 288. In addition, platform tub 30 includes outside corner surfaces 290 that confront corners 288 as shown in FIG. 9. Corners 288 and corner surfaces 290 are configured so that the air passing from the transverse head-end portion of air flow channel 148 into the longitudinal portions of air flow channel 148 and the air passing from the longitudinal portions of air flow channel 148 into the transverse foot-end portion of air flow channel 148 does not become turbulent. Thus, center divider 282 and the various surfaces and walls that bound air flow channel 148 cooperate to ensure that the flow of air through air flow channel 148 is substantially laminar.

Some of the air circulating through the longitudinal portions of air flow channel 148 passes upwardly through the air vent slots 276 that are adjacent to the longitudinal sides of mattress 32 to provide a pair of spaced-apart air curtains near the sides of the patient supported on mattress 32. Some of the air circulating in air flow channel 148 flows from the longitudinal portions thereof into the transverse portion of air flow channel 148 at the foot end of platform tub 30. The air in the transverse portion of air flow channel 148 moves upwardly through the air vent slots 276 at the foot end of platform cover 268 to provide an air curtain near the feet of the patient supported on mattress 32.

The portion of bottom wall 280 of platform tub 30 that is positioned to lie in first chamber 136 provides platform tub 30 with a horizontal planar datum surface 328 as shown in FIG. 9. Bottom wall 280 ramps upwardly along the path of air flow channel 148 with respect to datum surface 328 to compensate for the air that is lost from air flow channel 148 through the air vent slots 276 thereabove. Ramping bottom wall 280 in this manner causes the velocity at which air exits each air vent slot 276 to more closely approximate a target velocity.

Although the invention has been described in detail with reference to a certain preferred embodiment, variations and modifications exist within the scope and spirit of the invention as described and as defined in the following claims.

We claim:

1. A humidifier module for a patient-support apparatus including an opening into which the module is inserted, an electrical service connector, an air inlet port, and an air outlet port, the humidifier module comprising
  a water reservoir configured to hold water,
  a heater configured to heat the water,
  an air chamber with an air inlet port and an air exhaust port for mating with the air inlet and outlet ports of the patient-support apparatus, and an electrical connector for mating with the electrical service connector of the patient-support apparatus,
  whereby the patient-support apparatus is provided with a humidified environment for a patient when the humidifier module is inserted into the patient-support apparatus.

2. The humidifier module of claim 1, wherein the patient-support apparatus includes one or more external doors that normally close the opening of the patient-support apparatus and wherein the doors are opened by the insertion of the humidifier module into the patient-support apparatus.

3. The humidifier module of claim 2, wherein the patient-support apparatus includes one or more internal doors that normally close the air inlet and outlet ports of the patient-support apparatus and wherein the doors are opened by the insertion of the humidifier module into patient-support apparatus.

4. The humidifier module of claim 3, wherein the module includes at least one spill damper doors and wherein the at least one spill damper door acts as a stop for preventing hot water heated by the heater from spilling out of the module.

5. The humidifier module of claim 3, wherein the heater is located in a chamber below the water reservoir.

6. The humidifier module of claim 5, wherein the module includes a control valve that connects the reservoir and the heater and the control valve is actuatable between an opened configuration in which water flows from the reservoir to the heater and a closed configuration in which water is prevented from flowing from the reservoir to the heater.

7. The humidifier module of claim 2, wherein the module includes one or more spill damper doors and wherein the door or doors act as a stop for preventing hot water heated by the heater from spilling out of the module.

8. The humidifier module of claim 7, wherein the heater is located in a chamber below the water reservoir.

9. The humidifier module of claim 8, wherein the module includes a control valve that connects the reservoir and the heater and the control valve is actuatable between an opened configuration in which water flows from the reservoir to the heater and a closed configuration in which water is prevented from flowing from the reservoir to the heater.

10. The humidifier module of claim 2, wherein the heater is located in a chamber below the water reservoir.

11. The humidifier module of claim 10, wherein the module includes a control valve that connects the reservoir and the heater and the control valve is actuatable between an opened configuration in which water flows from the reservoir to the heater and a closed configuration in which water is prevented from flowing from the reservoir to the heater.

12. The humidifier module of claim 1, wherein the patient-support apparatus includes one or more internal doors that normally close the air inlet and outlet ports of the patient-support apparatus and wherein the doors are opened by the insertion of the humidifier module into patient-support apparatus.

13. The humidifier module of claim 12, wherein the module includes one or more spill damper doors and wherein the door or doors act as a stop for preventing hot water heated by the heater from spilling out of the module.

14. The humidifier module of claim 13, wherein the heater is located in a chamber below the water reservoir.

15. The humidifier module of claim 14, wherein the module includes a control valve that connects the reservoir and the heater and the control valve is actuatable between an opened configuration in which water flows from the reservoir to the heater and a closed configuration in which water is prevented from flowing from the reservoir to the heater.

16. The humidifier module of claim 12, wherein the heater is located in a chamber below the water reservoir.

17. The humidifier module of claim 16, wherein the module includes a control valve that connects the reservoir and the heater and the control valve is actuatable between an opened configuration in which water flows from the reservoir to the heater and a closed configuration in which water is prevented from flowing from the reservoir to the heater.

18. The humidifier module of claim 1, wherein the module includes one or more spill damper doors and wherein the door or doors act as a stop for preventing hot water heated by the heater from spilling out of the module.

19. The humidifier module of claim 18, wherein the heater is located in a chamber below the water reservoir.

20. The humidifier module of claim 19, wherein the module includes a control valve that connects the reservoir and the heater and the control valve is actuatable between an opened configuration in which water flows from the reservoir to the heater and a closed configuration in which water is prevented from flowing from the reservoir to the heater.

21. The humidifier module of claim 1, wherein the heater is located in a chamber below the water reservoir.

22. The humidifier module of claim 21, wherein the module includes a control valve that connects the reservoir and the heater and the control valve is actuatable between an opened configuration in which water flows from the reservoir to the heater and a closed configuration in which water is prevented from flowing from the reservoir to the heater.

23. The humidifier module of claim 1, wherein the module includes a control valve that connects the reservoir and the heater and the control valve is actuatable between an opened configuration in which water flows from the reservoir to the heater and a closed configuration in which water is prevented from flowing from the reservoir to the heater.

24. The humidifier module of claim 1, wherein a substantial portion of each of the water reservoir, the heater, and the air chamber pass through the opening of the patient-support apparatus as the humidifier module is inserted into the patient-support apparatus.

25. A patient-support apparatus comprising a base, a patient support supported above the base, the patient support being formed to include an opening, an air inlet port, and an air outlet port, an electrical service connector coupled to the patient support adjacent to the opening, and a humidifier module including a container for holding water and providing an air chamber above the water, the container including an air inlet port that mates with the air outlet port of the patient-support apparatus when the humidifier module is inserted into the opening so that air can move through the air outlet port of the patient-support apparatus and into the air chamber, the container including an air exhaust port that mates with the air inlet port of the patient-support apparatus when the humidifier module is inserted into the opening so that air can move out of the air chamber and through the air inlet port of the patient-support apparatus, and a heater for heating the water, the heater including an electrical connector that aligns with and automatically connects to the electrical service connector of the patient-support apparatus to receive power therefrom when the humidifier module is inserted into the opening, whereby the patient-support apparatus is provided with a humidified environment for a patient when the humidifier module is inserted into the patient-support apparatus.

26. The patient-support apparatus of claim 25, wherein the patient support further includes at least one door that normally closes the opening, insertion of the humidifier module through the opening opens the at least one door, and the at least one door closes automatically when the humidifier module is removed from the opening of the patient-support apparatus.

27. The patient-support apparatus of claim 26, wherein the at least one door includes a door that is opened by the electrical connector of the humidifier module when the humidifier module is inserted into the opening so that the electrical service connector of the patient-support apparatus is accessible to the electrical connector of the humidifier module.

28. The patient-support apparatus of claim 26, wherein the at least one door includes a first door that pivots about a first axis in a first direction when the humidifier module is inserted through the opening and a second door that pivots about a second axis in a second direction opposite to the first direction when the humidifier module is inserted through the opening.

29. The patient-support apparatus of claim 28, wherein the first axis and the second axis are both substantially vertical.

30. The patient-support apparatus of claim 25, wherein the humidifier module further includes a water reservoir adjacent to the container and configured to hold water separately from the container.

31. The patient-support apparatus of claim 30, wherein the humidifier module includes a control valve that couples the water reservoir to the container and the control valve is actuatable between an opened configuration in which water flows from the water reservoir to the container and a closed configuration in which water is prevented from flowing from the reservoir to the container.

32. The patient-support apparatus of claim 31, wherein the humidifier module includes a water level sensor that senses the level of the water in the container and provides a signal to the control valve to actuate the control valve between the opened and closed configurations.

33. The patient-support apparatus of claim 30, wherein a substantial portion of the water reservoir is positioned to lie inside the patient support while the humidifier module is inserted through the opening, the humidifier module further includes a refill door that is positioned to lie outside the patient support while the humidifier module is inserted through the opening, and the refill door can be opened to allow water to be poured into the water reservoir.

34. The patient-support apparatus of claim 25, wherein the patient-support apparatus is formed to include an aperture adjacent to the opening, the humidifier module further includes a locking pin, and the locking pin is movable between a locking position extended into the aperture to prevent the humidifier module from being removed from the opening and a releasing position retracted out of the opening to allow the humidifier module to be removed from the opening.

35. The patient-support apparatus of claim 34, wherein the humidifier module includes a solenoid coupled to the locking pin and the solenoid is actuatable to move the locking pin between the locking and releasing positions.

36. The patient-support apparatus of claim 35, wherein the humidifier module further includes a temperature sensor that senses the temperature of a surface of the humidifier module and provides a signal to the solenoid to actuate the solenoid to move the locking pin between the locking and releasing positions.

37. A humidifier module for a patient-support apparatus including an opening into which the module is inserted, an electrical service connector, an air inlet port, and an air outlet port, the humidifier module comprising a container for holding water and providing an air chamber above the water, the container including an air inlet port that mates with the air outlet port of the patient-support apparatus when the humidifier module is inserted into the opening so that air can move through the air outlet port of the patient-support apparatus and into the air chamber, the container including an air exhaust port that mates with the air inlet port of the patient-support apparatus when the humidifier module is inserted into the opening so that air can move out of the air chamber and through the air inlet port of the patient-support apparatus, and a heater for heating the water, the heater including an electrical connector that couples to the electrical service connector of the patient-support apparatus to receive power therefrom when the humidifier module is inserted into the opening, the heater being positioned to lie beneath the water to be heated, whereby the patient-support apparatus is provided with a humidified environment for a patient when the humidifier module is inserted into the patient support system.

38. The humidifier module of claim 37, wherein the heater includes a heater pan that holds water and a heater pad that heats the water and the heater pad is coupled to a bottom surface of the heater pan.

39. The humidifier module of claim 38, wherein the container includes a bottom wall and the heater pad is positioned to lie between the bottom surface of the heater pan and the bottom wall of the container.

40. The humidifier module of claim 37, further comprising a locking pin that locks the humidifier module to the patient-support apparatus when the heater temperature exceeds a threshold temperature and an indicator that indicates that the humidifier is locked to the patient-support apparatus.

41. A patient-support apparatus comprising a patient support including a fluid circulation system having a flow path along which circulated fluid is directed to provide a thermally controlled environment for a patient, a compartment for accepting a removable humidifier module, an inlet port in fluid communication with the compartment, and an outlet port in fluid communication with the compartment, a first door pivotably coupled to the patient support and normally closing the inlet port, a second door pivotably coupled to the patient support and normally closing the outlet port, and a humidifier module including a water container for containing water, an inlet port for connecting with the outlet port of the patient support when the humidifier module is inserted into the compartment, an exhaust port for connecting with the inlet port of the patient support when the humidifier module is inserted into the compartment, and first and second door openers arranged to engage and pivot the respective first and second doors to an opened position to allow at least some of the fluid in the flow path to be diverted through the humidifier module and over the water contained in the water container.

42. The patient-support apparatus of claim 41, wherein the patient support further includes a pivot pin and the first and second doors are both mounted on the pivot pin for pivoting movement.

43. The patient-support apparatus of claim 42, wherein the pivot pin extends vertically.

44. The patient-support apparatus of claim 43, wherein the first door opener is spaced apart from the second door opener to define a pin-receiving space therebetween and the pivot pin is positioned to lie in the pin-receiving space when the humidifier module is inserted into the compartment.

45. The patient-support apparatus of claim 43, wherein the first and second doors pivot in opposite directions toward one another as the first and second doors pivot in response to insertion of the humidifier module into the compartment.

46. The patient-support apparatus of claim 42, wherein the first and second doors pivot in opposite directions toward one another in response to insertion of the humidifier module into the compartment.

47. The patient-support apparatus of claim 42, wherein the patient support includes a wall portion spaced apart from the pivot pin to define an orifice therebetween, the circulated fluid flows through the orifice when the humidifier module is removed from the compartment, and at least one of the first and second doors extend between the wall portion and the pivot pin to close the orifice when the humidifier module is inserted into the compartment.

48. The patient-support apparatus of claim 41, wherein the humidifier module further includes a first spill damper door that closes the inlet port of the humidifier module when removed from the compartment and a second spill damper door that closes the exhaust port of the humidifier module when removed from the compartment.

49. The patient-support apparatus of claim 48, wherein the patient support further includes third and fourth door openers arranged to engage and move the respective first and second spill damper doors to open the inlet port and the exhaust port of the humidifier module when the humidifier module is inserted into the compartment.

50. The patient-support apparatus of claim 48, wherein the third and fourth door openers pivot the first and second spill damper doors upwardly relative to the water container as the humidifier module is inserted into the compartment.

51. The patient-support apparatus of claim 41, wherein the first door opener is positioned to lie beneath the inlet port of the humidifier module, the second door opener is positioned to lie beneath the exhaust port of the humidifier module, and each of the first and second door openers is formed to include a recess for catching water that spills out of the water container through the inlet and exhaust ports.

52. A patient-support apparatus comprising
- a patient support having a first chamber, a second chamber, and a fluid-flow orifice between the first and second chambers,
- a fan positioned to lie in the first chamber and operable to move fluid through the orifice into the second chamber, and
- laminar flow profile structure appended to the patient support in the second chamber and configured to maintain laminar flow of the fluid as the fluid enters the second chamber from the first chamber.

53. The patient-support apparatus of claim 52, wherein the patient support includes a pair of transverse walls and a pair of longitudinal walls that subdivide the second chamber into a mattress well and a channel that substantially encompasses the mattress well and the laminar profile structure is configured to direct substantially equivalent amounts of fluid along each of the longitudinal walls.

54. The patient-support apparatus of claim 53, wherein the laminar flow profile structure includes a center divider having an apex at the fluid-flow orifice and a pair of curved surfaces that extend from the apex and toward one of the transverse walls.

55. The patient-support apparatus of claim 54, further comprising a cover plate positioned to lie in the second chamber and the center divider is appended to and extends downwardly from the cover plate.

56. The patient-support apparatus of claim 53, wherein the patient support includes a platform tub in which the mattress well and channel are formed and a platform cover positioned to lie above the channel, the platform cover is formed to include a mattress-receiving aperture that mates with the mattress well and a plurality of vent slots that are arranged around the mattress-receiving aperture, and the vent slots are in fluid communication with the channel so that some of the fluid flowing in the channel passes upwardly through each of the vent slots.

57. The patient-support apparatus of claim 56, wherein the patient support includes a bottom wall having a datum surface in the first chamber and inclined surfaces in the second chamber, the inclined surfaces are positioned to lie in the channel, and the inclined surfaces are configured so that air exits each vent slot of the platform cover at a velocity that is close to a target velocity.

58. The patient-support apparatus of claim 56, further comprising a cover plate positioned to lie in the second chamber above the bottom wall and adjacent to one of the transverse walls and at least one of the vent slots being positioned to lie above the cover plate.

59. The patient-support apparatus of claim 58, wherein the cover plate is formed to include at least one bleeder hole that allows a portion of the fluid to pass upwardly therethrough toward the at least one vent slot that is positioned to lie above the cover plate.

60. The patient-support apparatus of claim 52, wherein the laminar flow profile structure includes a center divider configured to divert the fluid to flow along two separate paths within the patient support and the center divider is configured so that substantially equivalent amounts of fluid are diverted along each path.

61. The patient-support apparatus of claim 60, wherein the laminar flow profile structure further includes an apex at the orifice.

62. The patient-support apparatus of claim 61, wherein the center divider includes a pair of concave curved surfaces that extend from the apex through an angle of approximately 90°.

63. The patient-support apparatus of claim 60, further comprising a cover plate extending beyond opposite sides of the center divider.

64. A humidifier module for a patient-support apparatus including a fluid circulation system for circulating fluid and an opening into which the humidifier module is inserted, the humidifier module comprising
- a container for holding water and providing an air chamber above the water, the container including an air inlet and an air outlet, the fluid circulation system moving air through the air chamber,
- a heater for heating the water,
- a water reservoir for holding additional water,
- a control valve coupled to the water reservoir and coupled to the container, the control valve having a closed configuration blocking the flow of water from the water reservoir to the container and the control valve having an opened configuration allowing the flow of water from the water reservoir to the container, and
- a level sensor for sensing the water level in the container and providing a signal to the control valve to move the control valve between the opened and closed configurations.

65. The humidifier module of claim 64, wherein the level sensor is a refractive light sensor.

66. The humidifier module of claim 64, wherein the water reservoir is positioned to lie above the container and the additional water flows from the water reservoir to the container when the control valve is in the opened configuration due to gravity.

67. A patient-support apparatus comprising a patient support including a fluid circulation system for circulating fluid, a compartment for accepting a removable self-contained humidifier module, and a lock pin-receiving space adjacent to the compartment, a humidifier module comprising a container for holding water and providing an air chamber above the water, the fluid circulation system circulating fluid through the air chamber when the humidifier module is inserted into the opening, a heater for heating the water, a temperature sensor for sensing the temperature of a surface of the humidifier module, and a locking mechanism including a locking pin, the locking mechanism being coupled to the temperature sensor and configured to move the locking pin in response to the temperature sensed by the temperature sensor, the locking pin having an extended position received in the lock-pin receiving space to lock the humidifier module to the patient support when the temperature sensed exceeds a predetermined temperature, and the locking pin having a retracted position pulled out of the lock pin-receiving space to unlock the humidifier module from the patient support when the temperature sensed is below the predetermined temperature.

68. The patient-support apparatus of claim 67, wherein the locking mechanism includes a solenoid that is electrically actuated to move the locking pin between the extended and retracted positions.

69. The patient-support apparatus of claim 67, wherein the heater includes a heater pan and a heater pad and the temperature sensor is positioned to lie between the heater pan and the heater pad.

70. The patient-support apparatus of claim 67, wherein the patient support includes a platform tub in which the compartment is formed and a member adjacent to a portion of the compartment and the lock-pin receiving space is formed in the member.

71. The patient-support apparatus of claim 70, wherein the member extends over a portion of the compartment, the lock-pin receiving space is an aperture formed in the member, and the locking pin moves vertically into and out of the aperture.

* * * * *